US009581141B2

(12) United States Patent
Frey et al.

(10) Patent No.: US 9,581,141 B2
(45) Date of Patent: Feb. 28, 2017

(54) EARLY DETECTION OF WIND TURBINE DEGRADATION USING ACOUSTICAL MONITORING

(71) Applicant: Inventus Holdings, LLC, Juno Beach, FL (US)

(72) Inventors: Ann Frey, Port St. Lucie, FL (US); Frank Roark, Boca Raton, FL (US); Miguel Gonzalez, Jupiter, FL (US); Daniel M. Brake, Hobe Sound, FL (US)

(73) Assignee: Inventus Holdings, LLC, Juno Beach, FL (US)

( * ) Notice: Subject to any disclaimer, the term of this patent is extended or adjusted under 35 U.S.C. 154(b) by 519 days.

(21) Appl. No.: 14/077,327

(22) Filed: Nov. 12, 2013

(65) Prior Publication Data

US 2014/0133981 A1    May 15, 2014

Related U.S. Application Data

(60) Provisional application No. 61/725,743, filed on Nov. 13, 2012.

(51) Int. Cl.
| | | |
|---|---|---|
| *F03D 11/00* | (2006.01) | |
| *G01N 29/14* | (2006.01) | |
| *G01N 29/42* | (2006.01) | |
| *G01N 29/44* | (2006.01) | |

(52) U.S. Cl.
CPC .......... *F03D 11/0091* (2013.01); *F03D 17/00* (2016.05); *G01N 29/14* (2013.01); *G01N 29/42* (2013.01); *G01N 29/4427* (2013.01); *G01N 2291/2693* (2013.01); *Y02E 10/722* (2013.01)

(58) Field of Classification Search
CPC .... F03D 11/0091; G01N 29/14; G01N 29/42; G01N 29/4427; G01N 2291/2693; Y02E 10/722
See application file for complete search history.

(56) References Cited

U.S. PATENT DOCUMENTS

| | | | |
|---|---|---|---|
| 2009/0169378 A1* | 7/2009 | Menke | F03D 7/0224 416/1 |
| 2011/0135442 A1* | 6/2011 | Kerber | F03D 11/0091 415/1 |
| 2012/0166000 A1* | 6/2012 | Ellena | G05B 19/042 700/287 |

FOREIGN PATENT DOCUMENTS

JP        2007192828 A   *   8/2007

* cited by examiner

*Primary Examiner* — Igor Kershteyn
(74) *Attorney, Agent, or Firm* — Feldman Gale, P.A.

(57) ABSTRACT

Disclosed is a system and method for monitoring wind turbines, generally comprising a microphone for picking up acoustic emissions from a wind turbine and outputting a signal corresponding to the emissions; a filter for splitting the signal into a plurality of signals according to a plurality of frequency bands; and a processor for processing the plurality of signals and generating sound level data corresponding to at least a subset of the frequency bands. The system compares the sound level data with a sound threshold and generates an alarm signal when the sound level data exceeds the sound threshold. Alternatively, the system may include different thresholds corresponding to the different frequency bands, and an alarm can be generated when one or more of the different thresholds are exceeded by the different signals in the different frequency bands.

20 Claims, 4 Drawing Sheets

EARLY DETECTION OF WIND TURBINE DEGRADATION USING ACOUSTICAL MONITORING

CROSS REFERENCE TO RELATED APPLICATION

This application claims the benefit of U.S. Provisional Application No. 61/725,743, filed Nov. 13, 2012, the disclosure of which is hereby incorporated herein by reference in its entirety.

FIELD OF THE INVENTION

The present invention relates to a system and method for monitoring wind turbines. More particularly, the present invention relates to a system and method for detection of wind turbine degradation using acoustical monitoring.

BACKGROUND

Recently, wind turbines have received increased attention as an environmentally safe and relatively inexpensive alternative energy source. With this growing interest, considerable efforts have been made to develop wind turbines that are reliable and efficient.

Generally, a wind turbine includes a rotor having a rotatable hub assembly having multiple rotor blades. The rotor is mounted within a housing or nacelle, which is positioned on top of a truss or tubular tower. Utility grade wind turbines (i.e., wind turbines designed to provide electrical power to a utility grid) can have large rotors (e.g., 30 or more meters in diameter). Blades on these rotors transform wind energy into a rotational torque or force that drives one or more generators. The generators may be rotationally coupled to the rotor through a gearbox. The gearbox steps up the inherently low rotational speed of the turbine rotor for the generator to efficiently convert mechanical energy to electrical energy, which is fed into a utility grid.

Gearless direct drive wind turbines also exist. The rotor, generator, gearbox and other components are typically mounted within a housing, or nacelle, that is positioned on top of a tower.

Wind turbine components, such as bearings, gears, and/or rotor blades may become worn down or damaged over time. To detect such component damage, wind turbines often include a monitoring system that measures vibrations generated by the component during an operation of the wind turbine. Such monitoring systems may be complex and/or may require significant computational resources to extract component damage information from the measured vibrations.

Operational detriments may eventually cause suboptimal performance, whether temporarily (e.g., rotor blade icing) or indefinitely (e.g., structural damage to a rotor blade). At least some known methods of monitoring wind turbines detect operational detriments indirectly by detecting anomalies or symptoms, such as decreased power output and/or inoperability, of a wind turbine. Moreover, because many potential causes exist for such anomalies or symptoms, determining the root cause of an anomaly or symptom requires manual inspection by a service technician, introducing undesirable delay and expense before the root cause can be addressed. In view of the disadvantages associated with the current solutions, there is a need in the art for improved methods and systems for monitoring wind turbines.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In one embodiment, the system of the present invention includes one or more detection units, each detection unit having a microphone for detecting acoustic emissions from a wind turbine and outputting a signal corresponding to the emissions; a filtering device for splitting the signal into a plurality of signals according to a plurality of frequency bands; and a processor for processing the plurality of signals and generating sound level data corresponding to at least a subset of the frequency bands. In one embodiment, the disclosed system compares the sound level data with a first sound threshold and generates an alarm signal when the sound level data exceeds the first sound threshold. As used herein, the term "sound level" means sound volume.

Alternatively, the system may include a plurality of different sound thresholds, each threshold corresponding to a different frequency band. In this embodiment, an alarm can be generated when one or more of the plurality of thresholds is exceeded by sound signals in the different frequency bands.

In one embodiment, the detection unit including the microphone, the filtering device, and the processor may be integrated in an enclosure. One or more such enclosed detection units may be mounted on different locations of the wind turbine. For example, a first detection unit may be mounted at the base of a tower supporting the wind turbine; a second detection unit may be mounted on the middle section of the tower; and a third detection unit may be mounted on a nacelle of the wind turbine.

In one embodiment, the system includes a communications module that may communicate the sound level data over a network to a programmable logic controller ("PLC") or a supervisory control and data acquisition ("SCADA") server, and which may optionally be integrated in the enclosure housing the detection unit. In yet another embodiment, the processor may format the sound level data using a Modbus protocol before the communications module transmits the sound level data over the network.

The following description and the annexed drawings set forth in detail certain illustrative aspects of the invention. These aspects are indicative, however, of but a few of the various ways in which the principles of the invention may be employed and the present invention is intended to include all such aspects and their equivalents. Other advantages and novel features of the invention will become apparent from the following detailed description of the invention when considered in conjunction with the drawings.

DETAILED DESCRIPTION OF ILLUSTRATIVE EMBODIMENTS

Figure 1:
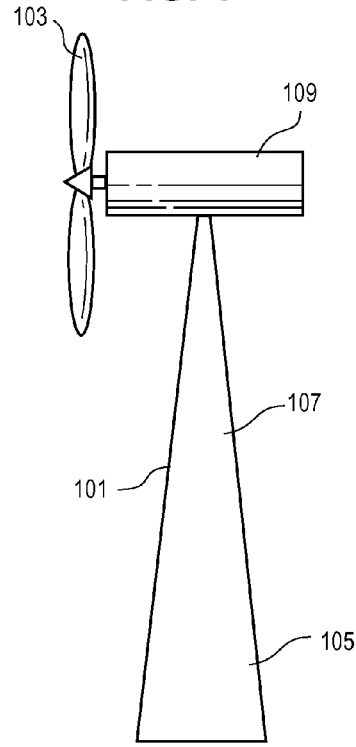
FIG. 1 illustrates a wind turbine having a tower base, middle section, and nacelle.

The following detailed description and the appended drawings describe and illustrate some embodiments of the invention for the purpose of enabling one of ordinary skill in the relevant art to make and use the invention. As such, the detailed description and illustration of these embodiments are purely illustrative in nature and are in no way intended to limit the scope of the invention, or its protection, in any manner. It should also be understood that the drawings are not to scale and in certain instances details have been omitted, which are not necessary for an understanding of the present invention, such as details of fabrication and assembly.

In accordance with one embodiment, a wind sound detection unit may include a microphone, a filter, a processor, and a communications module. Those elements may be integrated in a small enclosure. The detection unit may be mounted on different locations on the turbine which have access to a turbine communications network. In one embodiment, the wind sound detection unit may be placed on a lower section of a tower supporting the wind turbine if the turbine does not have network connectivity in the nacelle, for example. In one embodiment, the detection unit may be installed in the nacelle.

Through use of the microphone, the detection unit may detect acoustic emissions generated by the turbine. The acoustic emissions are filtered and processed by a processor to generate sound level data. The sound level data may be communicated using a communications module over a turbine network to a software program on a SCADA server or a dedicated PLC. The wind sound analysis may be done either in the detection unit or in a program in the SCADA server or in a dedicated PLC. The term "monitoring device" is used herein to refer to the PLC, SCADA, or any other monitoring device that runs the monitoring software.

A Modbus interface may also be used to configure the detection unit. Exemplary configuration parameters may include:

Network address.
Alarm levels of the frequency ranges, e.g., 20 frequency range alarm limits (the absolute minimum and maximum frequencies may be determined by the sensitivity of the selected microphone).
Configuring the system so that the Modbus IP communications interface is polled periodically (e.g., every 10 seconds) during operation, with the polled data including maximum sound level for each of the frequency ranges.
Resetting the maximum sound level to zero after each read or poll.
Setting the length of sound capture files (e.g., in seconds)
Calibration of the sound levels to compensate for variations in microphone sensitivity.

The configuration parameter related to resetting of maximum sound or volume level to zero is further explained. In one embodiment, to detect a maximum volume within a polling period, each poll resets all the detected maximum sound levels to zero.

In another embodiment, the length of sound capture files is configured. For example, the system may allow for real-time sound file creation by the detection unit. These captures will collect the microphone input to a WAV file for remote analysis.

In one embodiment, the wind sound detection unit may include a single circuit board mounted in a small enclosure. The circuit board may have the microphone mounted on it or the microphone may be mounted externally to the detection unit. The circuit board may also include a processor, a filtering device (for example, a digital signal processor ("DSP")), and the communications module (for example, an Ethernet connection interface). In one embodiment, by using the Modbus protocol as a communications standard, data collection and analysis may be implemented in a variety of ways. For example, sound analysis may be performed by software in the detection unit or a SCADA server or by a dedicated PLC connected to both the turbine network (for example, a LAN) and a control network (for example, a WAN). In another embodiment, sound analysis may be performed at the detection unit.

As illustrated in FIG. 1, one embodiment of the monitoring system of the present invention includes a tower 101 for supporting the wind turbine 103 and three wind sound detection units installed on a plurality of testing points (for collecting the sound samples). As illustrated in FIG. 1, testing points may be located on the tower base 105, a tower middle section 107, and the nacelle 109.

Figure 2:
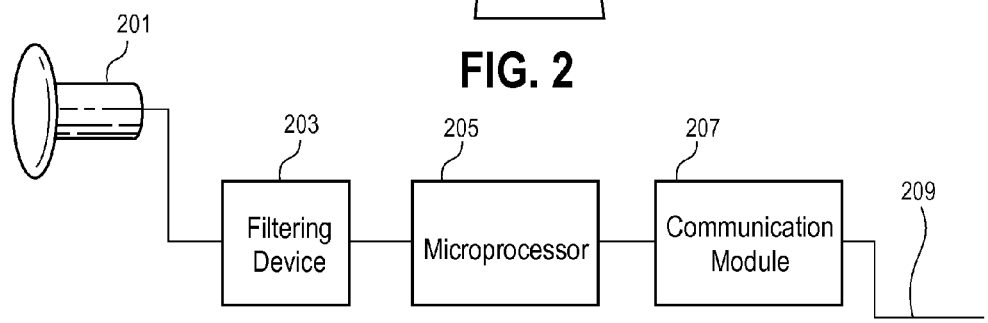
FIG. 2 illustrates a detection unit used in accordance with one embodiment.

As illustrated in FIG. 2, the wind sound detection unit may include a microphone 201, a filtering device 203, a processor 205, and a communications module 207 such as an Ethernet connection interface. In one embodiment, the filtering device 203, microprocessor 205, communications module 207, and/or the microphone 201 may be supplied with power and may exchange data through use of Power Over Ethernet ("POE") technology 209. In one embodiment, the filtering device 203 may be programmed to split the signal detected by the microphone 201 into a plurality of signals in accordance with different frequency bands, each of which will have a predetermined frequency range.

Figure 3:
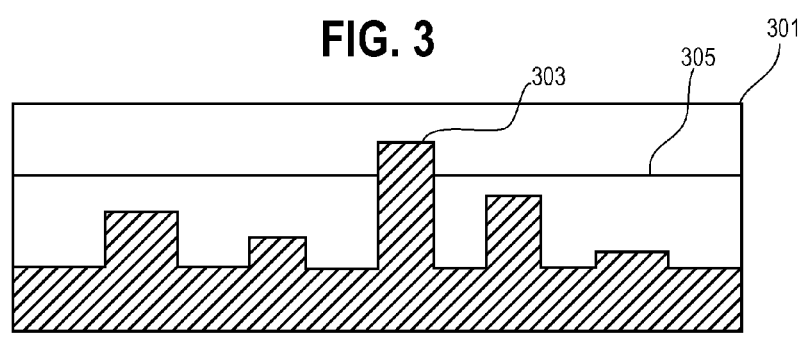
FIG. 3 illustrates a display of sound or noise levels detected at different frequency bands as well as a single sound or noise threshold for all frequency bands of interest in accordance with one embodiment.

As illustrated in FIG. 3, one embodiment also includes a display 301 of sound or noise levels detected at different frequency bands as well as a single sound or noise threshold for all frequency bands of interest. In the figure, noise or sound detected in one frequency band 303 exceeds the single sound threshold 305, which in one embodiment results in the generation of an alarm signal. In other embodiments of the invention, each frequency band may have an associated threshold which may vary or may be set depending on the frequency band.

Figure 4:
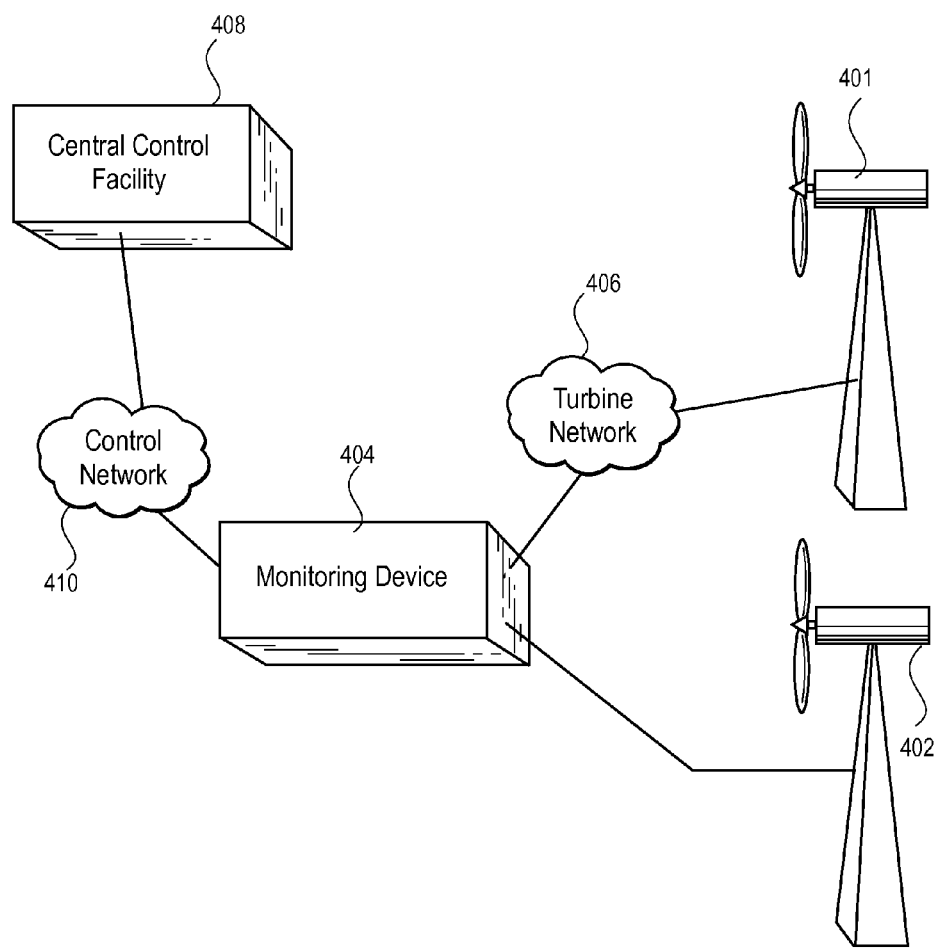
FIG. 4 illustrates a system for acoustical monitoring of wind turbines in accordance with one embodiment.

FIG. 4 illustrates a high level description of a monitoring system in accordance with one embodiment. The figure illustrates two different wind turbines, 401 and 402, in a wind farm, each turbine having two or more wind sound detection units. As illustrated, data may be exchanged between the detection units and a monitoring device 404 (for example, SCADA or PLC) over a turbine network 406 (for example, a LAN). As further depicted in FIG. 4, data is also exchanged between the monitoring device 404 and a central control facility 408 over a control network 410 (for example, a WAN). In one embodiment, the central control facility 408 sends commands to the monitoring device 404 to take corrective actions with respect to the operation of a wind turbine upon receipt of an alarm signal.

Figure 5:
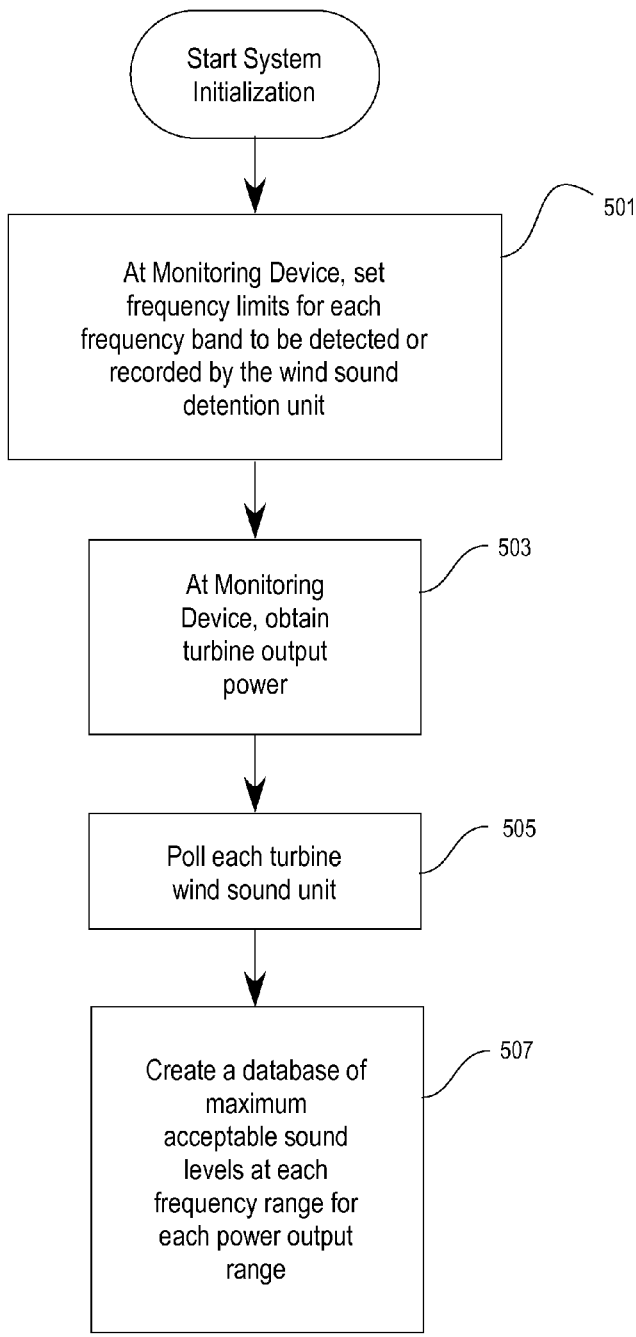
FIG. 5 illustrates a flowchart describing an initialization phase for a method for acoustical monitoring of wind turbines in accordance with one embodiment.

In accordance with illustrative embodiments, the sound analysis may be performed by software in the detection unit or in the SCADA server or by a dedicated PLC in two phases: 1) an initialization phase where the software learns what the normal sound levels are, or where the normal sound levels are determined for each of the frequency ranges and the alarm levels are preloaded into the detection units; and 2) an operation phase, where the turbines are monitored for variances from that normal level. For example, as illustrated in FIG. 5, at the initialization stage the software program run by the monitoring device may implement the following tasks:

Set the bandwidth for each of the frequency bands in the wind sound detection unit (step 501).

Obtain the turbine real time power output from the SCADA system (step 503).

Poll each turbine wind sound detection unit (step 505).

Create a database of maximum sound levels at each frequency range for each power output range, for example, at 50 kW resolution (step 507).

The creation of a database of maximum sound levels at each frequency range for each power output range is further explained. The expected sound levels may change depending on the turbine output power. A turbine at full generation is expected to emit more noise than a turbine at low generation. Thus, the system of the present invention may read the maximum sound levels generated in ranges of power generation with a 50 kW resolution. For example the system may read a first maximum sound level at a range of 0-50 kW; a second maximum sound level at a range of 51-100 kW; and a third maximum sound level at a range of 101-150 kW, and so on.

Figure 6:
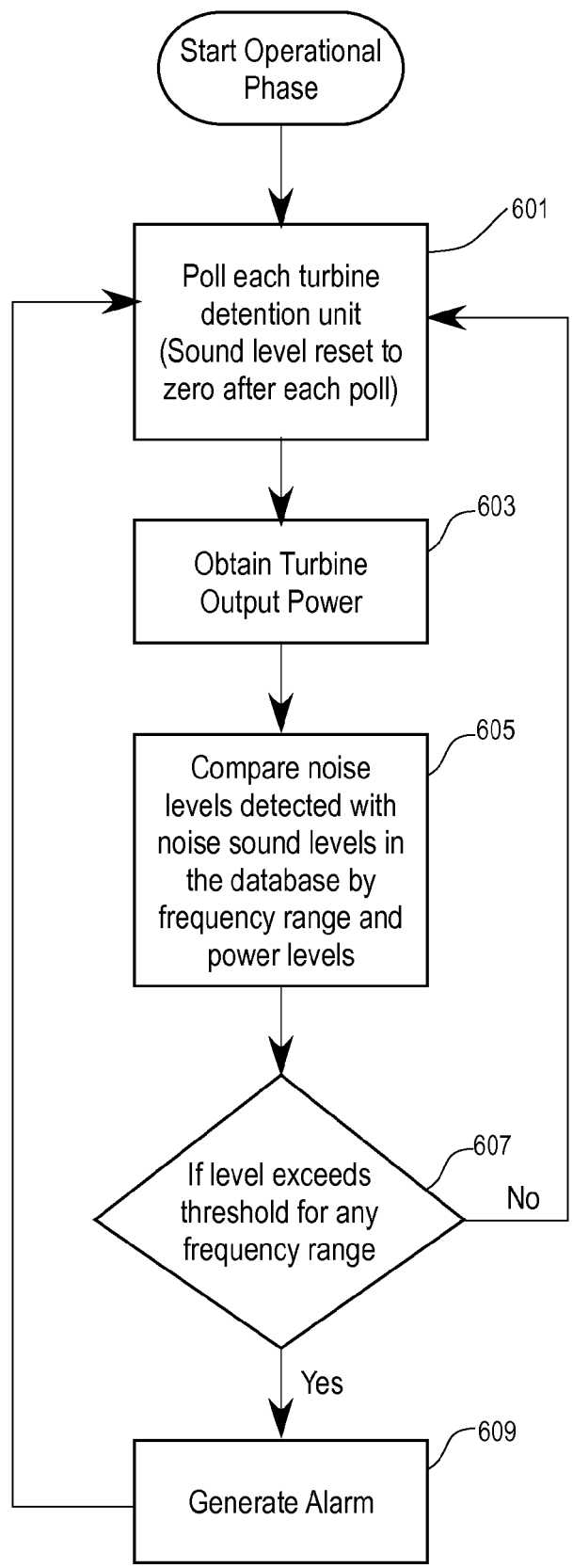
FIG. 6 illustrates a flowchart describing an operational phase for a method for acoustical monitoring of wind turbines in accordance with one embodiment.

At the conclusion of the initialization phase, the measured sound levels of each of the turbines may be checked against the others (of the same type of turbine) to detect any anomalous turbines. As illustrated in FIG. 6, in one embodiment, after completion of the initialization phase the software may be set to an operational phase to perform the following tasks:

Poll each turbine (e.g., all turbines in a wind farm or a subset thereof) wind sound detection unit every 10 seconds (step 601).

Obtain the turbine power output from the SCADA system (step 603).

Compare current noise levels against the noise or sound levels stored in a database by frequency and note any change from normal levels (step 605). This provides the ability to compare normal and abnormal readings for similar turbines across the fleet. The database may exist anywhere on the network, for example, at each turbine site or remotely.

Determine if noise level exceeded its normal sound levels for a defined period of time (step 607).

Generate alarms after a turbine has exceeded its normal sound levels for a defined period of time (step 609). For example, the alarm may go off if a single frequency band exceeds expected levels. A person of ordinary skill in the art would recognize that some types of failures will occur in a specific frequency range.

In one embodiment, the detection unit determines the frequency ranges associated with an alarm. Thus, instead of merely forwarding sound data to a PLC or SCADA, the detection units may perform the sound threshold comparisons.

In another embodiment, a WAV file is captured directly by the detection unit so that sound files are created in the detection unit, as opposed to having the detection units forward sound samples to the SCADA or PLC.

The present description of the invention makes reference to the use of SCADA systems and PLCs for monitoring and controlling the operation of wind turbines. In general, use of SCADA systems and PLCs to monitor wind turbines is known in the art. The present application incorporates by reference U.S. patent application Ser. No. 12/979,752 entitled "REMOTE WIND TURBINE RESET SYSTEM AND METHOD." That application, incorporated herein by reference in its entirety, discloses the use of programmable logic controllers ("PLCs") and Supervisory Control and Data Acquisition ("SCADA") systems to monitor and control wind turbines.

The descriptions set forth above are meant to be illustrative and not limiting. Various modifications of the invention, in addition to those described herein, will be apparent to those skilled in the art from the foregoing description. Such modifications are also intended to fall within the scope of the concepts described herein.

The foregoing description of possible implementations consistent with the present invention does not represent a comprehensive list of all such implementations or all variations of the implementations described. The description of only some implementation should not be construed as an intent to exclude other implementations. For example, artisans will understand how to implement the invention in many other ways, using equivalents and alternatives that do not depart from the scope of the invention. Moreover, unless indicated to the contrary in the preceding description, none of the components described in the implementations are essential to the invention.

The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods.

What is claimed is:

1. A system for monitoring a wind turbine comprising one or more detection units, each detection unit comprising:

a microphone for picking up acoustic emissions from said wind turbine and outputting a signal corresponding to said acoustic emissions;

a filtering device for splitting said signal into a plurality of signals according to a plurality of frequency bands; and a processor for processing said plurality of signals and generating sound level data corresponding to at least a subset of said plurality of frequency bands;

wherein said sound level data are analyzed as a function of a real time power output level of said wind turbine.

2. The system of claim 1, wherein said detection unit is integrated in a small enclosure.

3. The system of claim 1, wherein said wind turbine is supported by a tower and said detection unit is mounted at the base of said tower.

4. The system of claim 1, wherein said detection unit is mounted on a nacelle of said wind turbine.

5. The system of claim 1, further comprising a communications module to communicate said sound level data over a network to a programmable logic controller.

6. The system of claim 5, wherein said processor formats said sound level data using a Modbus protocol before communicating said sound level data to said programmable logic controller.

7. The system of claim 1, further comprising a communications module to communicate said sound level data over a network to a SCADA server.

8. The system of claim 7, wherein said processor formats said sound level data using a Modbus protocol before communicating said sound level data to said SCADA server.

9. The system of claim 5, wherein said programmable logic controller or said detection unit is configured to compare said sound level data with a first sound threshold and generate an alarm signal when said sound level data exceeds said first sound threshold.

10. The system of claim 9, wherein said first sound threshold corresponds to a maximum sound level generated by said wind turbine at said real time power output level.

11. The system of claim 9, wherein said first sound threshold corresponds to a first frequency band from said plurality of frequency bands, and further comprising a second threshold corresponding to a second frequency band from the plurality of frequency bands, and wherein said programmable logic controller or said detection unit generates an alarm signal when said sound level data corresponding to said first frequency band exceeds said first sound threshold or when sound level data corresponding to said second frequency band exceeds said second threshold.

12. The system of claim 7, wherein said SCADA server or said detection unit is configured to compare said sound level data with a first sound threshold and generate an alarm signal when said sound level data exceeds said first sound threshold.

13. The system of claim 12, wherein said first sound threshold corresponds to a maximum sound level generated by said wind turbine at said real time power output level.

14. The system of claim 12, wherein said first sound threshold corresponds to a first frequency band from the plurality of frequency bands, and further comprising a second threshold corresponding to a second frequency band from the plurality of frequency bands, and wherein said SCADA server generates an alarm signal when sound level data corresponding to said first frequency band exceeds said first threshold or when said sound level data corresponding to said second frequency band exceeds said second threshold.

15. The system of claim 1, wherein said plurality of frequency bands include a low frequency boundary and a high frequency boundary determined by a sensitivity of said microphone.

16. The system of claim 1, wherein said system comprises a plurality of wind turbines and said sound level data are collected from each of said plurality of wind turbines, and wherein said detection unit is configured to compare said sound level data with a first sound threshold corresponding to a maximum sound level generated by said plurality of wind turbines at said real time power output level and to generate an alarm signal when particular sound level data for a particular wind turbine exceed said first sound threshold.

17. The system of claim 16, wherein said sound level data for a particular one of said plurality of wind turbines are analyzed as a function of a real time power output level of each of said plurality of wind turbines.

18. The system of claim 17, wherein said sound level data are analyzed to identify abnormal operation of ones of said plurality of wind turbines.

19. A method for monitoring a wind turbine having one or more detection units, each said detection unit comprising a microphone for picking up acoustic emissions from said wind turbine and outputting a signal corresponding to said acoustic emissions, a filtering device for splitting said signal into a plurality of signals according to a plurality of frequency bands, and a processor for processing said plurality of signals and generating sound level data corresponding to at least a subset of said plurality of frequency bands, said method comprising:
  setting the bandwidth for each of said plurality of frequency bands;
  obtaining the real time power output range for said wind turbine from a SCADA server or programmable logic controller in communication with said detection unit;
  polling said detection unit;
  creating a database of maximum sound levels at each said frequency band for each said power output range; and
  determining degradation of said wind turbine by comparing said sound level data with said maximum sound levels in accordance with a real time power output level of said wind turbine.

20. A method for monitoring a wind turbine having one or more detection units, each said detection unit comprising a microphone for picking up acoustic emissions from said wind turbine and outputting a signal corresponding to said acoustic emissions, a filtering device for splitting said signal into a plurality of signals according to a plurality of frequency bands, and a processor for processing said plurality of signals and generating sound level data corresponding to at least a subset of said plurality of frequency bands, said method comprising:
  polling said wind turbine at repeating time intervals;
  obtaining the real time power output range for said wind turbine from a SCADA server or programmable logic controller in communication with said detection unit;
  comparing a sound level detected by said detection unit against a sound level stored in a database by frequency;
  determining if said sound level detected by said detection unit exceeded a normal sound level corresponding to a real time power output level of said wind turbine for a defined period of time; and
  generating alarms if said sound level detected by said detection unit exceeds said normal sound level.

* * * * *